United States Patent [19]
Dairoku et al.

[11] Patent Number: 5,422,405
[45] Date of Patent: Jun. 6, 1995

[54] METHOD FOR PRODUCTION OF ABSORBENT RESIN

[75] Inventors: Yorimichi Dairoku; Kinya Nagasuna; Kazutaka Yano; Toru Yanase; Yoshihiko Masuda, all of Hyogo, Japan

[73] Assignee: Nippon Shokubai Co., Ltd., Osaka, Japan

[21] Appl. No.: 167,077

[22] Filed: Dec. 15, 1993

[30] Foreign Application Priority Data

Dec. 16, 1992 [JP] Japan .................. 4-336392

[51] Int. Cl.$^6$ ................................ C08F 8/14
[52] U.S. Cl. ................... 525/384; 525/324.5; 525/330.1; 525/330.6
[58] Field of Search ............................ 525/384

[56] References Cited

U.S. PATENT DOCUMENTS

| | | | |
|---|---|---|---|
| 4,061,846 | 12/1977 | Gross et al. | 525/384 |
| 4,587,308 | 5/1986 | Makita et al. | 525/373 |
| 4,666,975 | 5/1987 | Yamasaki et al. | 525/384 |
| 4,880,868 | 11/1989 | Le-Khac | 525/384 |
| 5,032,628 | 7/1991 | Choi et al. | 523/409 |
| 5,055,501 | 10/1991 | Moriya et al. | 523/409 |
| 5,164,459 | 11/1992 | Kimura et al. | 525/384 |

FOREIGN PATENT DOCUMENTS

| | | |
|---|---|---|
| 0317106 | 5/1989 | European Pat. Off. |
| 0509708A1 | 10/1992 | European Pat. Off. |
| 2559158 | 8/1985 | France |
| 2606414 | 5/1988 | France |
| WO91/15368 | 10/1991 | WIPO |

*Primary Examiner*—Bernard Lipman
*Attorney, Agent, or Firm*—Burns, Doane, Swecker & Mathis

[57] ABSTRACT

A method for the production of an absorbent resin retaining at a high level an absorption capacity without load, one of the basic physical properties of absorbent resin, and excelling in an absorption capacity under load is provided. The production is attained by mixing an absorbent resin as a base polymer possessing a carboxyl group with a first cross-linking agent possessing a solubility parameter (SP value) of not less than 12.5 $(cal/cm^3)^{\frac{1}{2}}$ and exhibiting reactivity with the carboxyl group and a second cross-linking agent possessing a solubility parameter (SP value) of less than 12.5 $(cal/cm^3)^{\frac{1}{2}}$ and exhibiting reactivity with the carboxyl group and then subjecting the resultant mixture to a heat treatment at a temperature not less than 160° C.

15 Claims, 1 Drawing Sheet

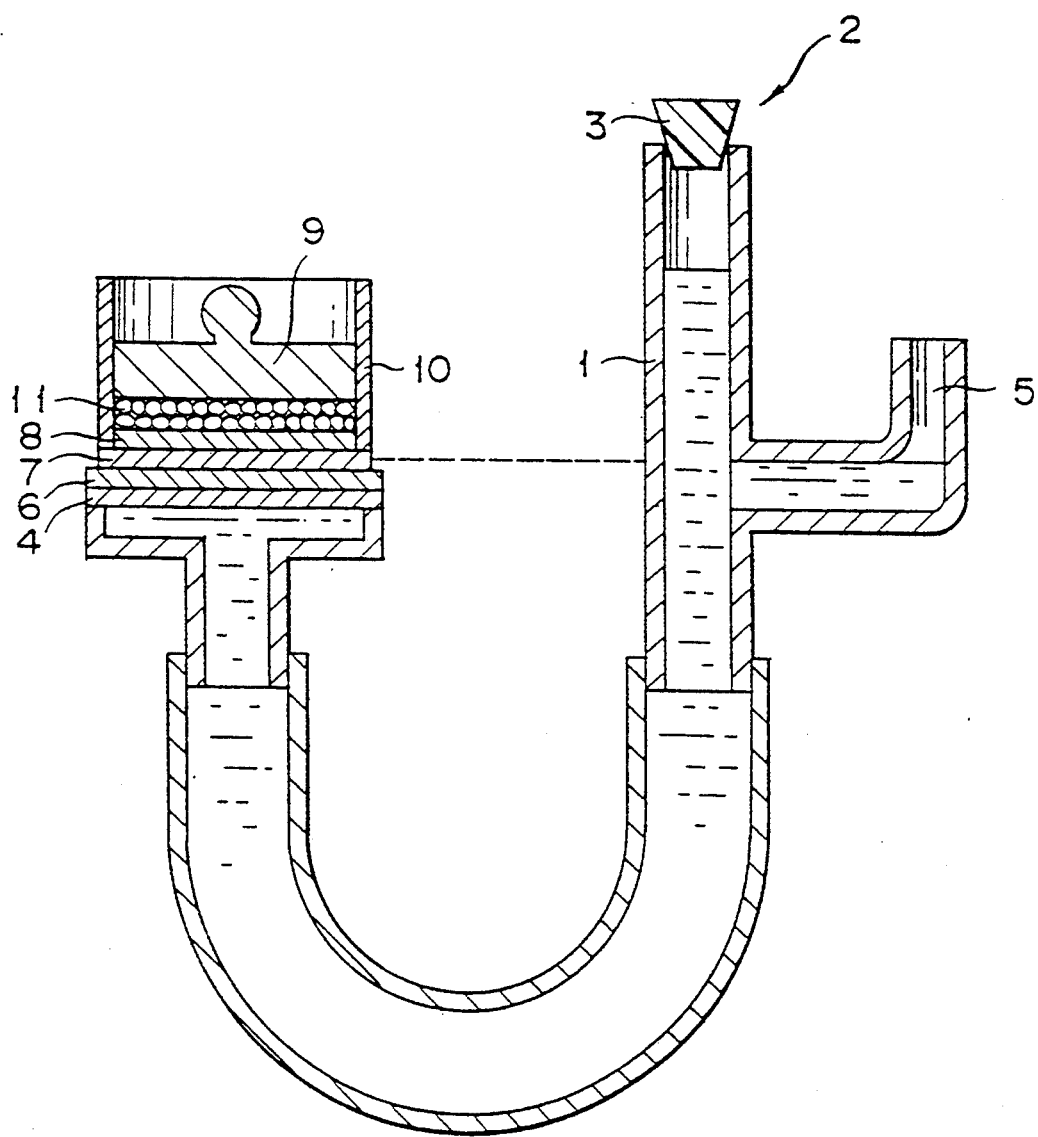
FIGURE

METHOD FOR PRODUCTION OF ABSORBENT RESIN

BACKGROUND OF THE INVENTION

1. Field of the Invention

This invention relates to a method for the production of an absorbent resin. More particularly, it relates to a method for the production of an absorbent resin which exhibits high level of absorption capacity under load as well as absorption capacity without load and, when used in a sanitary material, manifests a particularly excellent quality.

2. Description of the Prior Art

Absorbent resins have been finding extensive utility in recent years as one of the component substances for such sanitary materials as disposable diapers and sanitary napkins which are intended for the absorption of bodily humors.

The absorbent resins which have been known in the art include partially neutralized cross-linked polyacrylic acids (JP-A-SHO-55-84,304, JP-A-SHO-55-108,407, and JP-A-SHO-55-133,413), hydrolyzates of starch-acrylonitrile graft polymers (JP-A-SHO-46-43,995), neutralized starch-acrylic acid graft polymer (JP-A-SHO-51-125,468), saponified vinyl acetate-acrylic ester copolymers (JP-A-SHO-52-14,689), hydrolyzed acrylonitrile copolymers or acrylamide copolymers (JP-A-SHO-53-15,959) or cross-linked products of such hydrolyzates, and cross-linked cationic monomers (JP-A-SHO-58-154,709 and JP-A-SHO-58-154,710), for example.

The absorbent resins are desired to excel in such characteristic properties as the absorption capacity, the absorption rate, the liquid permeability, the gel strength and the suction power to absorb liquid from a substrate containing the aqueous liquid, for example. These characteristic properties, however, do not necessarily show a positive correlation. Such physical properties as liquid permeability, gel strength, and absorption rate, for example, decline in accordance with the increase of absorption capacity.

As means for conferring an ideally balanced improvement on the various absorption properties of an absorbent resin, the technique of cross-linking the surface region of the absorbent resin has been known to the art. Various methods for working this technique have been proposed to date.

For example, as a cross-linking agent, the method using a polyhydric alcohol (JP-A-SHO-58-180,233 and JP-A-SHO-61-16,903), the method using a polyglycidyl compound, a polyaziridine compound, a polyamine compound, or a polyisocyanate compound (JP-A-SHO-59-189,103), the method using glyoxal (JP-A-SHO-52-117,393), the method using a polyvalent metallic element (JP-A-SHO-51-136,588, JP-A-SHO-61-257,235, and JP-A-SHO-62-7,745, the method using a silane coupling agent (JP-A-SHO-61-211,305, JP-A-SHO-61-252,212, and JP-A-SHO-61-264,006), the method using an epoxy compound and a hydroxy compound (JP-A-HEI-2-132,103), and the method using an alkylene carbonate (DE-4020780) have been known in the art. Besides these methods, during the cross-linking reaction, the method using the presence of an inert inorganic powder (JP-A-SHO-60-163,956 and JP-A-SHO-60-255,814), the method using the presence of a dihydric alcohol (JP-A-HEI-1-292,004), the method using the presence of water and an ether compound (JP-A-HEI-2-153,903), etc. have been also known.

These methods indeed bring about a perceptibly balanced improvement of the physical properties of an absorbent resin. The improvement, however, can hardly be called sufficient. The absorbent resins are still in need of a further improvement in quality. Particularly in recent years, the desirability of an absorbent resin which retains at a high level the absorption capacity without load, one of the basic physical properties of the conventional absorbent resin, and meanwhile excels in absorption properties under load, particularly the absorption capacity under load, has come to find growing recognition. Naturally, the absorption capacity without load and the absorption capacity under load are generally in a contradictory relation. In fact, the heretofore known techniques for cross-linking the surface region of an absorbent resin are such that they cannot fully satisfy this desirability.

It is, therefore, an object of this invention to provide a method for the production of an aborbent resin.

Another object of this invention is to provide a method for production of an absorbent resin which exhibits high level of absorption capacity under load as well as absorption capacity without load and, when used in a sanitary material, manifests a particularly excellent quality.

SUMMARY OF THE INVENTION

The objects described are accomplished by a method for the production of an absorbent resin which comprises mixing an absorbent resin as a carboxyl group-containing base polymer with a first cross-linking agent possessing a solubility parameter (SP value) of not less than 12.5 $(cal/cm^3)^{\frac{1}{2}}$ and exhibiting reactivity with the carboxyl group and a second cross-linking agent possessing a solubility parameter (SP value) of less than 12.5 $(cal/cm^3)^{\frac{1}{2}}$ and exhibiting reactivity with the carboxyl group and heat-treating the resultant mixture at a temperature of not less than 160° C.

We have made a diligent study with a view to further improving the absorption properties of absorbent resin thereby accomplishing the objects described above and consequently found that a resin which retains various absorption properties, especially the absorption capacity without load at a high level and meanwhile exhibits a preeminently excellent absorption capacity under load is obtained by mixing an absorbent resin with two or more cross-linking agents having different solubility parameters and treating the resultant mixture at a temperature in a specific range. This invention has been perfected as a result.

By the method of this invention, a resin which retains at a high level the absorption capacity without load, one of the basic physical properties of absorbent resin, and meanwhile excels in absorption properties under load, particularly the absorption capacity under load, can be produced easily and conveniently.

The absorbent resin of this invention is advantageously used particularly in such sanitary materials as disposable diapers and sanitary napkins because it exhibits a high absorption capacity without load, preeminently excels in the absorption capacity under load.

BRIEF DESCRIPTION OF THE DRAWING

FIGURE is a cross section of a device used in this invention for the measurement of absorption capacity under load.

EXPLANATION OF THE PREFERRED EMBODIMENT

Now, this invention will be explained more specifically below.

The absorbent resin which can be used as a base polymer in this invention belongs to the heretofore known resins of the kind sharing the ability to absorb a large volume of water and form a hydrogel. It must be possessed of a carboxyl group. The resins which answer this description include partially neutralized cross-linked polyacrylic acid, hydrolyzed starch-acrylonitrile graft polymer, partially neutralized starch-acrylic acid graft polymer, saponified vinyl acetate-acrylic ester copolymers, hydrolyzed acrylonitrile copolymers or acrylamide copolymers or cross-linked products of such modified carboxyl group-containing cross-linked polyvinyl alcohol, and cross-linked isobutylene-maleic acid copolymer, for example.

These absorbent resins as a base polymer are generally obtained by polymerizing a monomer component containing essentially at least one member selected from the group of such unsaturated carboxylic acids as, for example, acrylic acid, methacrylic acid, maleic acid, maleic anhydride, fumaric acid, crotonic acid, itaconic acid, $\beta$-acryloxy propionic acid, and products of neutralization thereof. Among monomer components mentioned above, acrylic acid, methacrylic acid, and products of neutralization thereof prove particularly preferable.

For the production of the absorbent resin as the base polymer in this invention, the unsaturated carboxylic acid may be polymerized, when necessary, in conjunction with other monomer. As typical examples of the other monomer just mentioned, anionic unsaturated monomers and salts thereof such as vinyl sulfonic acid, styrene sulfonic acid, 2-(meth)acrylamide-2-methylpropane sulfonic acid, 2-(meth)acryloylethane sulfonic acid, and 2-(meth)acryloylpropane sulfonic acid; nonionic hydrophilic group-containing unsaturated monomers such as acrylamide, methacrylamide, N-ethyl (meth)acrylamide, N-n-propyl-(meth)acrylamide, N-isopropyl-(meth)acrylamide, N,N-dimethyl-(meth)acrylamide, 2-hydroxyethyl-(meth)acrylate, 2-hydroxypropyl-(meth)acrylate, methoxy polyethylene glycol-(meth)-acrylate, polyethylene glycol mono(meth)acrylate, vinyl pyridine, N-vinyl pyrrolidone, N-acryloyl piperidine, and N-acryloyl pyrrolidine; and cationic unsaturated monomers such as N,N-dimethyl aminoethyl-(meth)acrylate, N,N-diethylaminoethyl-(meth)acrylate, N,N-dimethylaminopropyl-(meth)acrylate, N,N-dimethylaminopropyl-(meth)acrylamide, and quaternary salts thereof may be cited.

The amount of the carboxyl group contained by the absorbent resin as the base polymer is not particularly limited. It is, however, desired to be not less than 0.01 equivalent weight of carboxyl group, based on 100 g of the absorbent resin as the base polymer. In the case of a partially neutralized cross-linked polyacrylic acid, for example, the proportion of the unneutralized polyacrylic acid is desired to be in the range of 1 to 60 mol %, more preferably in the range of 10 to 50 mol %.

The absorbent resin as the base polymer is produced more preferably by causing the monomer component to copolymerize or react with a very small amount of an internal cross-linking agent containing at least two polymerizable unsaturated groups or at least two reactive groups than by causing the monomer component to cross-link in itself without using any external cross-linking agent.

As typical examples of the internal cross-linking agent, N,N'-methylenebis(meth)acrylamide, (poly)ethylene glycol di(meth)acrylate, (poly)propylene glycol di(meth)acrylate, trimethylolpropane tri(meth)acrylate, glycerol tri(meth)-acrylate, glycerol acrylate methacrylate, ethylene oxide-modified trimethylolpropane tri(meth)acrylate, pentaerythritol-tetra-(meth)acrylate, pentaerythritol hexa(meth)acrylate, triallyl cyanurate, triallyl isocyanurate, triallyl phosphate, triallyl amine, poly(meth)allyloxy alkanes, (poly)ethylene glycol diglycidyl ether, glycerol diglycidyl ether, ethylene glycol, polyethylene glycol, propylene glycol, pentaerythritol, ethylene diamine, polyethylene imine, and glycidyl (meth)acrylate may be cited. Optionally, these internal cross-linking agents may be used in the form of a mixture of two or more members. On account of various factors such as, for example, the absorption properties of the produced absorbent resin, it is preferable to use essentially the internal cross-linking agent as a compound having at least two polymerizable unsaturated groups. The amount of this compound to be used in the range of 0.005 to 2 mol %, preferably 0.01 to 1 mol %, based on the amount of the monomer component mentioned above.

When the monomer component mentioned above is polymerized for the production of the absorbent resin as the base polymer in this invention, this polymerization may be carried out in the form of bulk polymerization or precipitation polymerization. In the light of the quality of the final product and the ease of control of the polymerization, however, it is preferable to prepare the monomer component in the form of an aqueous solution and subject the aqueous solution to solution polymerization or reversed-phase suspension polymerization.

To be used advantageously in this invention, the absorbent resin as the base polymer which is obtained by the method of polymerization mentioned above is in the shape of amorphous fragments, beads, fibers, rods, roughly spherical granules, or similars. In the light of such factors as the ability to diffuse liquid and the resistance to migration in or separation from pulp which are attendant on the use of absorbent resin in sanitary materials, the absorbent resin as the base polymer obtained by solution polymerization in the form of amorphous fragments having an average particle diameter in the range of 100 to 1,000 $\mu$m, preferably in the range of 300 to 600 $\mu$m proves most desirable.

Further, the absorbent resin as the base polymer can be handled as powder when the water content thereof is in the range of 1 to 50% by weight, preferably 1 to 20% by weight, and more preferably 1 to 10% by weight. If the water content exceeds 50% by weight, the possibility ensues that the first cross-linking agent and the second cross-linking agent to be used in this invention will deeply permeate the particles of the absorbent resin as the base polymer to the extent of not only degrading the absorption capacity but also preventing the improvement of the absorption properties under load of the produced absorbent resin.

The first cross-linking agent which can be used in this invention is required to possess a solubility parameter (SP value) of 12.5 $(cal/cm^3)^{\frac{1}{2}}$ and exhibit reactivity with a carboxyl group. The solubility parameter (SP value) is used generally as a factor representing the polarity of a given compound. This invention adopts the numerical value of the solubility parameter $\delta$ $(cal/cm^3)^{\frac{1}{2}}$ of solvent reported in the "Polymer Handbook," third edition (Wiley Interscience Corp), VII-527 to 539. For a cross-linking agent which is not included in the table, this invention proposes to adopt the numerical value $\delta$ (cal/cm$^3$)$^{\frac{1}{2}}$ which is derived by substituting the Hoy's cohesive energy constant reported in VII-525 ibidem in the Small's formula found in VII-524 ibidem.

As typical examples of the first cross-linking agent which possesses such a solubility parameter (SP value) of not less than 12.5 [(cal/cm$^3$)$^{\frac{1}{2}}$] and exhibits reactivity with a carboxyl group, ethylene glycol, propylene glycol, glycerol, polyglycerol, pentaerythritol, sorbitol, ethylene carbonate, propylene carbonate, etc. may be cited. One member or a mixture of two or more members selected from among these examples may be used effectively. Preferably, this solubility parameter (SP value) is in the range of 13.0 to 18.0 (cal/cm$^3$)$^{\frac{1}{2}}$.

The second cross-linking agent which is effectively usable in this invention must possess a solubility parameter (SP value) of less than 12.5 (cal/cm$^3$)$^{\frac{1}{2}}$ and exhibit reactivity with a carboxyl group. As typical examples of the second cross-linking agent, diethylene glycol, triethylene glycol, tetraethylene glycol, dipropylene glycol, tripropylene glycol, 1,3-butanediol, 1,4-butanediol, 1,5-pentanediol, 2,4-pentanediol, 1,6-hexanediol, 2,5-hexanediol, trimethylol propane, diethanolamine, triethanolamine, ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, ethylene diamine, diethylenetriamine, triethylenetetramine, 2,4-tolylene diisocyanate, hexamethylene diisocyanate, 4,5-dimethyl-1,3-dioxolan-2-on, epichlorohydrin, and epibromohydrin may be cited. One member or a mixture of two or more members selected from among these cross-linking agents can be used effectively herein. Preferably, the solubility parameter (SP value) is in the range between not less than 9.5 (cal/cm$^3$)$^{\frac{1}{2}}$ and less than 12.0 (cal/cm$^3$)$^{\frac{1}{2}}$.

As the cross-linking agent for this invention, it is necessary to use at least one member selected from the group of typical examples of the first cross-linking agent and at least one member selected from the group of typical examples of the second cross-linking agent cited above. The production of an absorbent resin excellent in absorption properties under load which is aimed at by this invention cannot be attained by the sole use of one species of the first cross-linking agent or one species of the second cross-linking agent or by the combined use of two or more members selected from either the group of first cross-linking agents or the group of second cross-linking agents cited above.

The selection of the first and second cross-linking agents is preferable to be such that the difference between the solubility parameter (SP value) of the first cross-linking agent and the solubility parameter (SP value) of the second cross-linking agent is not less than 2 (cal/cm$^3$)$^{\frac{1}{2}}$. If the difference of the two solubility parameters (SP values) is less than 2 (cal/cm$^3$)$^{\frac{1}{2}}$, the possibility arises that the effect to be derived from the use of these two species of cross-linking agent will not be easily manifested and the improvement of absorption properties under load will be attained with difficulty. Preferably, the selection of the first and second cross-linking agents is such that the difference of the solubility parameter (SP value) of the first cross-linking agent and the solubility parameter (SP value) of the second cross-linking agent is not less than 3 (cal/cm$^3$)$^{\frac{1}{2}}$.

The first cross-linking agent is preferable to have a molecular weight of not more than 200 and the second cross-linking agent to have a molecular weight of not more than 350. If the molecular weight of the first cross-linking agent exceeds 200, the possibility ensues that the first cross-linking agent will not permeate the particles of the absorbent resin as the base polymer deeply through the surface thereof but tend to stagnate in the surface region thereof and the absorption properties of the produced absorbent resin under load will be improved with difficulty. If the molecular weight of the second cross-linking agent exceeds 350, the possibility arises that this second cross-linking agent will only sparingly permeate the particles of the absorbent resin as the base polymer and the absorption properties of the produced absorbent resin under load will be improved only with difficulty. Preferably, the first cross-linking agent has a molecular weight in the range of 50 to 150 and the second cross-linking agent a molecular weight in the range of 150 to 300.

The amounts of the first and second cross-linking agents to be used in this invention are variable with the particular kinds of these cross-linking agents to be adopted. Generally, the amount of the first cross-linking agent is in the range of 0.001 to 10 parts by weight and that of the second cross-linking agent in the range of 0.001 to 10 parts by weight, respectively based on 100 parts by weight of the solids of the absorbent resin as the base polymer. If the amounts of the first and second cross-linking agents both exceed 10 parts by weight, their excesses not only prove wasteful but also fail to make any contribution to the accomplishment of the optimum effect of cross-linking aimed at by this invention. Conversely, if their amounts are less than 0.001 part by weight, the effect of improving the various absorption properties under load is attained with difficulty. Ideally, the amount of the first cross-linking agent is in the range of 0.01 to 8 parts by weight, preferably 0.1 to 5 parts by weight and that of the second cross-linking agent is in the range of 0.001 to 1 part by weight, preferably 0.005 to 0.5 part by weight.

When the absorbent resin as the base polymer is mixed with the first and second cross-linking agents, the present invention prefers the mixture to proceed in the presence of water. The amount of water to be used for the sake of this mixture in the present invention is variable with the kind, particle size, and water content of the absorbent resin to be used as the base polymer. Generally, this amount is not more than 10 parts by weight, preferably in the range of 0.5 to 5 parts by weight, based on 100 parts by weight of the solids of the absorbent resin as the base polymer.

This invention permits use of a hydrophilic organic solvent for the sake of the mixture of the absorbent resin as the base polymer with the first and second cross-linking agents. As typical examples of the hydrophilic organic solvent which is used effectively herein, lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethyl formamide; and sulfoxides such as dimethyl sulfoxide may be cited. The optimum amount of the hydrophilic organic solvent to be optionally used in this invention is variable with the kind and the particle size of the absorbent resin as the base polymer. Generally, this amount is not more than 20 parts by weight, preferably in the range of 1 to 10 parts by weight, based on 100 parts by weight of the solids of the absorbent resin as the base polymer.

This invention permits the mixture of the absorbent resin as the base polymer with the first and second cross-linking agents to proceed in an organic solvent in which the absorbent resin as the base polymer had been dispersed in advance. For the purpose of enabling the absorption properties under load obtained by this invention to be manifested to the highest possible advantage, it is preferable to adopt the method that the first and second cross-linking agents (and it necessary water and/or the hydrophilic organic solvent) is directly sprayed or added dropwise to the absorbent resin as the base polymer. When water is used for the sake of the mixture, water-insoluble fine powders may be present at the site of this mixture.

A device to be ideally used for the sake of this mixture must generate a large mixing power to ensure homogeneous mixture of the components. Typical examples of the mixing device which is used effectively in this invention include cylindrical mixing devices, double-wall conical mixing devices, V-shaped mixing devices, ribbon type mixing devices, screw-type mixing devices, fluidized bed rotary disk type mixing devices, air current type mixing devices, twin-arm type kneaders, internal mixing devices, rotary type mixing devices, and screw type extruding devices, for example.

In the present invention, the mixture resulting from the mixture of the absorbent resin as the base polymer with the first and second cross-linking agents is subsequently heated to effect cross-linking of the surface region of the particles thereof.

In this invention, the heat treatment to be performed after the addition of the cross-linking agents adopts a temperature of not less than 160° C. If the temperature of this heat treatment is less than 160° C., the heat treatment consumes an unduly long time and entails a sacrifice of productivity and the uniformity of cross-linkage owing to the use of both the first and second cross-linking agents is not accomplished and, consequently, the production of an absorbent resin excelling in absorption properties under load aimed at by this invention is not attained. The temperature of the heat treatment is desired to be in the range of 170° to 230° C., preferably 180° to 220° C.

The heat treatment can be carried out by the use of a conventional drying device or heating furnace. As concrete examples of the heating device, groove type mixing-drying devices, rotary drying devices, desk drying devices, fluidized-bed drying devices, air current drying devices, and infrared drying devices may be cited.

The absorbent resin which is produced by the method of this invention exhibits heretofore unattainable excellent physical properties such as, for example, an absorption capacity without load of 45 (g/g) with respect to physiological saline solution and an absorption capacity under load of 30 (ml/g) with respect to artificial urine.

Heretofore, the problem has prevailed that the absorption capacity without load is increased at a sacrifice of the absorption capacity under load and, conversely, the absorption capacity under load is increased at a sacrifice of the absorption capacity without load. The absorption resin produced by this invention exhibits excellent absorption properties both without load and under load. Though the mechanism which causes this excellent effect of the present invention remains yet to be elucidated, it may be logically explained by a postulate that since the absorbent resin as the base polymer is mixed with at least two species of cross-linking agent having different solubility parameters and the resultant mixture is subjected to cross-linking at a temperature in the specific range, the distribution of the two cross-linking agents in the surface region of the particles of the absorbent resin is optimized and the cross-linking reaction of two cross-linking agents is accelerated, with the result that cross-linked layer having a specific density gradient heretofore never attained by the conventional method are formed in the surface region or its vicinity of the particles. Further, when the absorbent resin as the base polymer to be used in this invention has the form of amorphous fragments as described above, the produced absorbent resin acquires, in addition to the excellent absorption properties mentioned above, the ability to diffuse liquid therein and repress migration thereof in or separation thereof from pulp, i.e. the quality never found in the known absorbent resins. This absorption resin, therefore, is ideally used for sanitary materials.

Optionally, the absorbent resin to be produced by this invention is allowed to incorporate therein such additives as deodorant, spice, inorganic powder, foaming agent, pigment, dye, hydrophilic filaments, fertilizer, oxidizing agent, reducing agent, water, and salts to acquire new functions.

Now, this invention will be described more specifically below with reference to working examples. It should be noted, however, that the scope of this invention is not limited to these working examples. The physical properties of the hydrophilic resin to be described in the working examples represent data which have been determined by the methods shown below.

The properties of the absorbent resin have been determined by the following methods.

(a) Absorption capacity (without load)

This property was determined by uniformly placing 0.2 g of a given absorbent resin in a teabag-like pouch (40×150 mm) of nonwoven fabric, immersing the pouch containing the sample in an aqueous 0.9 wt % sodium chloride solution (physiological saline solution), removing the wet pouch from the solution after 30 minutes' standing therein, allowing the solution to strain out of the wet pouch for a prescribed length of time, weighing the pouch to find the weight ($W_1$), repeating the same procedure while avoiding use of the absorbent resin, finding the weight ($W_0$) of the wet pouch, and performing the calculation of the following formula 1.

Absorption capacity (g/g)=(Weight $W_1$ after absorption (g)−Weight $W_0$ of blank (g))/(Weight of absorbent resin (g))     (1)

(b) Absorption capacity under load

With the aid of an apparatus constructed as illustrated in FIGURE, this property was determined by plugging an upper mouth 2 of a buret 1 with a stopper 3, setting a measuring base 4 and an air inlet 5 at an equal level, placing a filter paper 7 on a glass filter 6 of a diameter of 70 mm located in the central part of the measuring base 4, fixing a non-woven fabric 8 at the lower terminal part of a supporting cylinder 10 of a diameter of 55 mm, uniformly scattering 0.2 g of a given absorbent resin 11 on the non-woven fabric 8, placing a load of 20 g/cm$^2$ on the scattered sample 11, mounting the total of non-woven fabric, absorbent resin, and load as held in the supporting cylinder on the filter paper 7 spread on the glass fiber 6, allowing artificial urine (containing 1.9% of urea, 0.8% of NaCl, 0.1% of $CaCl_2$, and 0.1% of $MgSO_4$) to be absorbed by the absorbent resin for 30 minutes thereby finding the volume (A ml) of the artificial urine so absorbed, and performing the calculation of the following formula 2.

Absorption capacity under load (ml/g)=A (ml)/0.2 (g)        (2)

(c) Suction power

This magnitude was determined by pouring 20 ml of artificial urine over tissue paper thereby preparing a substrate material containing the artificial urine, placing 1 g of a given absorbent resin on the tissue paper and, after the elapse of 10 minutes, collecting a swollen gel, and weight the gel thereby finding suction power (g/g).

(d) Amount of liquid absorbed by a model diaper under load

This magnitude, i.e. the amount of artificial urine absorbed by a model diaper under load, was determined by securing a commercially available infant disposable diaper (L size), removing the core of the diaper, inserting as a replacement therefor a core having 7.5 g of a given absorbent resin buried in 30 g of a wad of pulp thereby completing a test diaper ($W_0$ g), keeping the test diaper immersed for 60 minutes in artificial urine kept under a load of 20 $g/cm^2$, removing the wet diaper from the artificial urine, straining the urine out of the wet diaper, weighing the diaper to find the weight ($W_1$ g), and finding the amount of the artificial urine (g) absorbed by this model diaper under load mentioned above by subtracting $W_0$ from $W_1$.

Referential Example

In 5,500 g of an aqueous solution of sodium acrylate having a neutralization ratio of 75 mol % (monomer concentration 33%), 1.58 g of N,N′-methylene bis-acrylamide as a cross-linking agent was dissolved. The aqueous solution was deaerated with nitrogen gas for 30 minutes and supplied to a lidded reaction vessel having an inner volume of 10 liters and provided with a jacketed stainless steel twin-arm kneader fitted with two sigma vanes and left standing therein at a temperature of 30° C., with the reaction system displaced with nitrogen.

Then, the monomer in the reaction vessel, after the elapse of one minute following the addition thereto of 2.4 g of ammonium persulfate and 0.12 g of 1-ascorbic acid, began to polymerize. After 16 minutes of the polymerization, the peak temperature in the reaction system reached 83° C. and the hydrated gel polymer was divided into particles about 5 mm in diameter. The stirring of the contents of the reaction vessel was further continued. After 60 minutes of the polymerization, the hydrated gel polymer was extracted from the reaction vessel.

The minute particles of hydrated gel polymer thus obtained were spread on a metallic net of 50 mesh and dried with hot air at 150° C. for 90 minutes. The dried particles were pulverized with a shaking mill and further classified with a 20-mesh screen. Consequently, an absorbent resin (1) having an average particle diameter of 400 μm was obtained as a base polymer.

EXAMPLE 1

A mixed cross-linking agent solution containing 1 part of glycerol (SP value δ=16.5) as a first cross-linking agent, 0.05 part of ethylene glycol diglycidyl ether (SP value δ=10.2) as a second cross-linking agent, 3 parts of water, and 1 part of ethyl alcohol was mixed with 100 parts of the absorbent resin (1) obtained as a base polymer in Referential Example 1. The resultant mixture was heat-treated at 195° C. for 40 minutes. The produced absorbent resin (1) was tested for quality. The results are shown in Table 1.

EXAMPLE 2

A mixed cross-linking agent solution containing 2 parts of ethylene carbonate (SP value δ=14.7) as a first cross-linking agent, 0.1 part of glycerol polyglycidyl ether (SP value δ=10.8 ) as a second cross-linking agent, 4 parts of water, and 1 part of isopropyl alcohol was mixed with 100 parts of the absorbent resin obtained as a base polymer in Referential Example 1. The resultant mixture was heat-treated at 180° C. for 60 minutes. The produced absorbent resin (2) was tested for quality. The results are shown in Table 1.

EXAMPLE 3

A mixed cross-linking agent solution containing 3 parts of propylene glycol (SP value δ=12.6) as a first cross-linking agent, 0.1 part of propylene glycol diglycidyl ether (SP value δ=10.1) as a second cross-linking agent, 5 parts of water, and 2 parts of methanol was mixed with 100 parts of the absorbent resin obtained as a base polymer in Referential Example 1. The resultant mixture was heat-treated at 195° C. for 40 minutes. The produced absorbent resin (3) was tested for quality. The results are shown in Table 1.

EXAMPLE 4

A mixed cross-linking agent solution containing 2 parts of ethylene glycol (SP value δ=14.6) as a first cross-linking agent, 0.1 part of diethylene triamine (SP value δ=10.7) as a second cross-linking agent, 2 parts of water, and 1 part of isopropyl alcohol was mixed with 100 parts of the absorbent resin (1) obtained as a base polymer in Referential Example 1. The resultant mixture was heat-treated at 180° C. for 60 minutes. The produced absorbent resin (4) was tested for quality. The results are shown in Table 1.

Control 1

A mixed cross-linking agent solution containing 1 part of glycerol (SP value δ=16.5), 3 parts of water, and 1 part of ethyl alcohol was mixed with 100 parts of the absorbent resin (1) obtained as a base polymer in Referential Example 1. The resultant mixture was heat-treated at 195° C. for 40 minutes. The produced absorbent resin (1) for comparison was tested for quality. The results are shown in Table 1.

Control 2

A mixed cross-linking agent solution containing 0.05 part of ethylene diglycidyl ether (SP value δ=10.2), 3 parts of water, and 1 part of ethyl alcohol was mixed with 100 parts of the absorbent resin (1) obtained as a base polymer in Referential Example 1. The produced absorbent resin (2) for comparison was tested for quality. The results are shown in Table 1.

Control 3

A mixed cross-linking agent solution containing 1 part of glycerol (SP value δ=16.5) as a first cross-linking agent, 0.05 part of ethylene glycol diglycidyl ether (SP value δ=10.2) as a second cross-linking agent, 3 parts of water, and 1 part of ethyl alcohol was mixed with 100 parts of the absorbent resin (1) obtained as a base polymer in Referential Example 1. The resultant mixture was heat-treated at 140° C. for 40 minutes. The produced absorbent resin (3) for comparison was tested for quality. The results are shown in Table 1.

Control 4

A mixed cross-linking agent solution containing 1 part of 1,3-butanediol (SP value δ11.6), 0.05 part of ethylene glycol diglycidyl ether (SP value δ=10.2), 3 parts of water, and 1 part of ethyl alcohol was mixed with 100 parts of the absorbent resin (1) obtained as a base polymer in Referential Example 1. The resultant mixture was heat-treated at 195° C. for 40 minutes. The produced absorbent resin (4) for comparison was tested for quality. The results are shown in Table 1.

Control 5

A mixed cross-linking agent solution containing 1 part of glycerol (SP value δ=16.5), 2 parts of ethylene carbonate (SP value δ=14.7), 5 parts of water, and 1 part of ethyl alcohol was mixed with 100 parts of the absorbent resin (1) obtained as a base polymer in Referential Example 1. The resultant mixture was heat-treated at 195° C. for 40 minutes. The produced absorbent resin (5) for comparison was tested for quality. The results are shown in Table 1.

TABLE 1

|  | Absorption capacity (without load) (g/g) | Absorption capacity under load (ml/g) | Suction power (g/g) | Amount of liquid absorbed by a model diaper under load (g) |
| --- | --- | --- | --- | --- |
| Absorbent resin (1) | 51 | 33 | 18 | 598 |
| Absorbent resin (2) | 53 | 32 | 17 | 587 |
| Absorbent resin (3) | 52 | 30 | 18 | 572 |
| Absorbent resin (4) | 48 | 31 | 17 | 579 |
| Absorbent resin (1) for comparison | 46 | 28 | 17 | 549 |
| Absorbent resin (2) for comparison | 55 | 27 | 16 | 543 |
| Absorbent resin (3) for comparison | 54 | 27 | 15 | 546 |
| Absorbent resin (4) for comparison | 55 | 26 | 15 | 538 |
| Absorbent resin (5) for comparison | 48 | 28 | 16 | 547 |

What is claimed is:

1. A method for the production of an absorbent resin which comprises mixing an absorbent resin as a base polymer possessing a carboxyl group with a first cross-linking agent possessing a solubility parameter (SP value) of not less than 12.5 $(cal/cm^3)^{\frac{1}{2}}$ and exhibiting reactivity with said carboxyl group and a second cross-linking agent possessing a solubility parameter (SP value) of less than 12.5 $(cal/cm^3)^{\frac{1}{2}}$ and subjecting the resultant mixture to a heat treatment at a temperature of not less than 160° C.

2. A method according to claim 1, wherein said first cross-linking agent has a solubility parameter (SP value) in the range of 13.0 to 18.0 $(cal/cm^3)^{\frac{1}{2}}$.

3. A method according to claim 1, wherein said second cross-linking agent has a solubility parameter (SP value) in the range of from not less than 9.5 $(cal/cm^3)^{\frac{1}{2}}$ to less than 12.0 $(cal/cm^3)^{\frac{1}{2}}$.

4. A method according to claim 1, wherein said first and second cross-linking agents are selected so that the difference between the solubility parameter (SP value) of said first cross-linking agent and the solubility parameter (SP value) of said second cross-linking agent is not less than 2 $(cal/cm^3)^{\frac{1}{2}}$.

5. A method according to claim 1, wherein said first cross-linking agent has a molecular weight of not more than 200 and said second cross-linking agent has a molecular weight of not more than 350.

6. A method according to claim 1, wherein the amount of said first cross-linking agent is in the range of 0.001 to 10 parts by weight and that of said second cross-linking agent in the range of 0.001 to 10 parts by weight, both based on 100 parts by weight of the solids of said absorbent resin as a base polymer.

7. A method according to claim 1, wherein said mixture is carried out in the presence of not more than 10 parts by weight of water based on 100 parts by weight of solids of said absorbent resin as a base polymer.

8. A method according to claim 1, wherein the amount of said carboxyl group of said absorbent resin as a base polymer is not less than 0.01 equivalent weight per 100 g of said absorbent resin.

9. A method according to claim 1, wherein said absorbent resin as a base polymer is a partially neutralized cross-linked polyacrylic acid and the proportion of the unneutralized polyacrylic acid is in the range of 1 to 60 mol %.

10. A method according to claim 1, wherein the water content of said absorbent resin as a base polymer is in the range of 1 to 10% by weight.

11. A method according to claim 7, wherein said mixture is carried out in the presence of 0.5 to 5 parts by weight of water based on 100 parts by weight of the solids of said absorbent resin as a base polymer.

12. A method according to claim 1, wherein the amount of said first cross-linking agent is in the range of 0.01 to 8 parts by weight and that of said second cross-linking agent in the range of 0.001 to 1 part by weight, both based on 100 parts by weight of the solids of said absorbent resin as a base polymer.

13. A method according to claim 1, wherein said heat treatment is carried out at a temperature in the range of 170° to 230° C.

14. A method according to claim 1, wherein the amount of said first cross-linking agent is in the range of 0.1 to 5 parts by weight and that of said second cross-linking agent in the range of 0.005 to 0.5 part by weight, both based on 100 parts by weight of the solids of said absorbent resin as a base polymer.

15. A method for the production of an absorbent resin comprising preparing a partially cross-linked base polymer possessing a carboxyl group, then mixing said base polymer with a first cross-linking agent possessing a solubility parameter of not less than 12.5 $(cal/cm^3)^{\frac{1}{2}}$ and exhibiting reactivity with said carboxyl group and a second cross-linking agent possessing a solubility parameter of less than 12.5 $(cal/cm^3)^{\frac{1}{2}}$ and subjecting the resultant mixture to a heat treatment at a temperature of not less than 160° C. to produce an absorbent resin having a cross-linked layer with a density gradient.

* * * * *